(12) United States Patent
Hickok

(10) Patent No.: US 7,060,302 B1
(45) Date of Patent: Jun. 13, 2006

(54) METAL-CONTAINING COMPOSITIONS, PREPARATIONS AND USES

(75) Inventor: Stephen Spaulding Hickok, London (GB)

(73) Assignee: Remedy Research Limited, London (GB)

( * ) Notice: Subject to any disclaimer, the term of this patent is extended or adjusted under 35 U.S.C. 154(b) by 398 days.

(21) Appl. No.: 10/070,062

(22) PCT Filed: Aug. 31, 2000

(86) PCT No.: PCT/GB00/03364

§ 371 (c)(1),
(2), (4) Date: Feb. 27, 2002

(87) PCT Pub. No.: WO01/15554

PCT Pub. Date: Mar. 8, 2001

(30) Foreign Application Priority Data

Aug. 31, 1999 (GB) .................................. 9920539.5
Nov. 30, 1999 (GB) .................................. 9928337.6

(51) Int. Cl.
*A61K 33/24* (2006.01)
*A61K 33/34* (2006.01)
*A61K 33/32* (2006.01)
*A61K 33/26* (2006.01)
*A61K 33/06* (2006.01)

(52) U.S. Cl. .................. 424/617; 424/630; 424/641; 424/646; 424/682; 424/702

(58) Field of Classification Search ................ 424/600, 424/617, 630, 641, 646, 682, 702
See application file for complete search history.

(56) References Cited

FOREIGN PATENT DOCUMENTS

| DE | 1211749 | * | 9/1962 |
|---|---|---|---|
| DE | 3208609 | * | 9/1983 |
| GB | 1111929 | | 5/1968 |
| JP | 5023585 | | 2/1993 |
| JP | 6128789 | | 5/1994 |
| JP | 11001436 | | 1/1999 |
| SU | 533678 | | 10/1976 |
| SU | 1787773 | | 1/1993 |

* cited by examiner

*Primary Examiner*—Alton Pryor
(74) *Attorney, Agent, or Firm*—Fay, Sharpe, Fagan, Minnich & McKee, LLP

(57) ABSTRACT

A metal-containing composition substantially comprising (i) at least one water soluble metal compound which forms metal ions when dissolved in water, (ii) at least one metal ion modifier as herein defined, (iii) at least one acid, and (iv) water said composition having a pH of less than 6 and an electrolytic potential in excess of 10 millivolts. Such compositions have uses in the prevention and/or treatment of pathogenic disease or disorder, as foodstuff supplements, in the treatment by disinfection of meat and other foodstuffs, in the coating, sealing and plating of metals, and treatment of water and sewage.

21 Claims, 4 Drawing Sheets

METAL-CONTAINING COMPOSITIONS, PREPARATIONS AND USES

Figure 1:
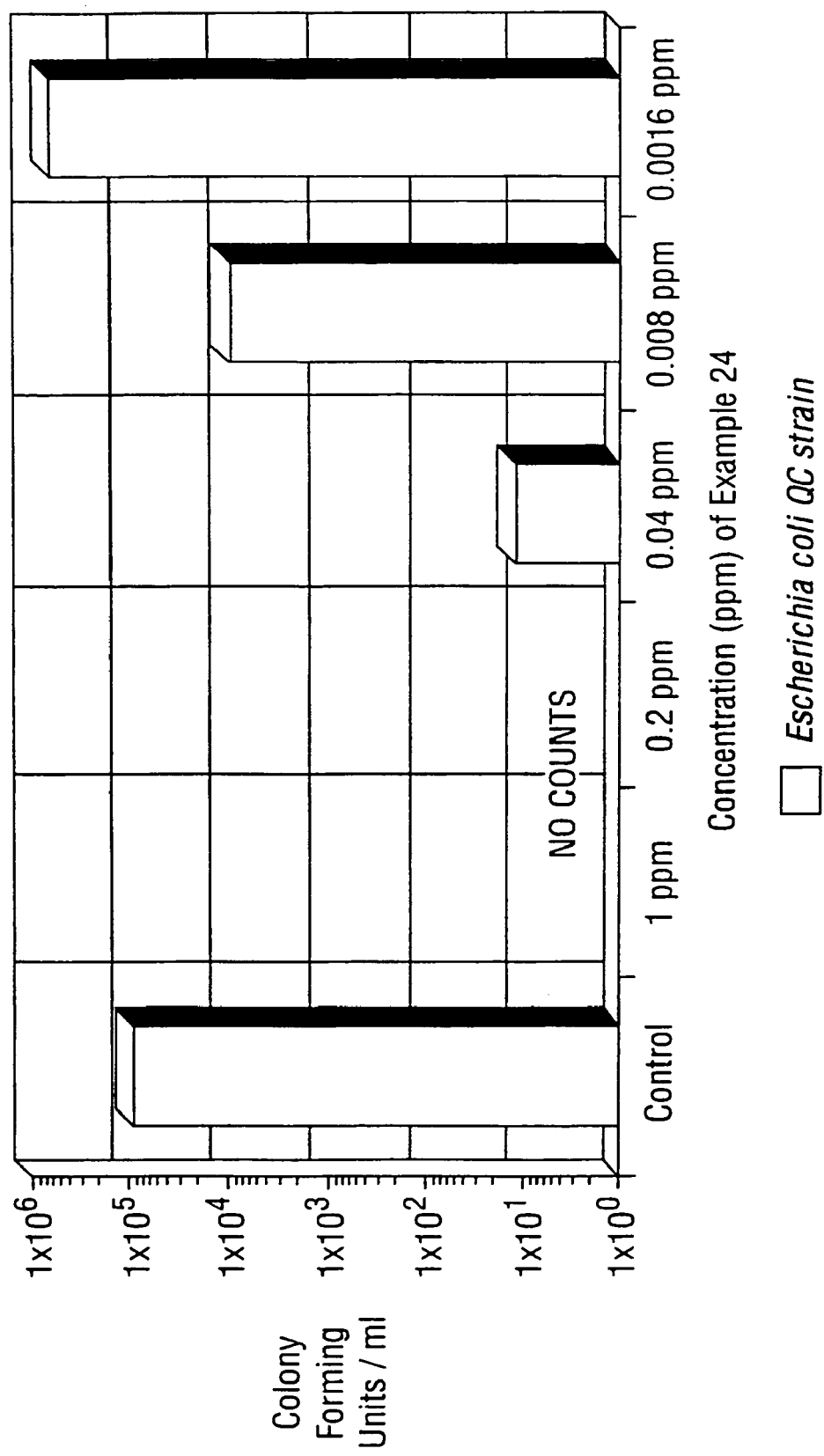

It is well established that minerals i.e. (races of selected metal elements are required as part of the human diet for good health. Mineral deficiencies can lead to poor health and specific disorders. Amongst the minerals that the body requires, there are, for example, the metals zinc, magnesium, copper, iron, and selenium. The human body requires traces of such minerals in soluble form whereby the corresponding metallic ions are bio-available within the bloodstream.

With the increase in highly processed and convenience foods, there are concerns that the typical diet in today's conditions may not contain sufficient vitamins and/or minerals. Accordingly vitamin and mineral supplements are widely available without prescription on the basis that they are foodstuff components and not medicaments.

This invention is particularly concerned with mineral metal compositions, their preparation and uses within a mineral 'delivery' system for humans or animals. It is known that mineral salts by themselves, e.g. zinc sulphate, iron sulphate and the like will dissociate in aqueous solution to form the corresponding ions e.g. $Zn^{2+}$ and $Fe^{2+}$ with $SO_4^{2-}$. However, it has been observed that the metallic mineral ions in solution within the bloodstream are not readily bio-available in the sense of being available for uptake by cells. Accordingly there are at least two mineral 'binder' systems available for enhancing bio-availability of these ions. Most mineral supplement compositions presently available are based upon an inorganic chelate binder system. In such compositions, the required mineral element e.g. zinc, magnesium or the like is chemically bonded to a chelate such that bio-availability of the mineral ions is still significantly impaired. The digestive system has difficulty in leaching the mineral element away from the chelate binder for cellular uptake. This limits their bio-availability. Chelate based mineral supplements apparently limit the body's absorption of the elemental mineral to some 7 to 10% of that presented. It is suggested that the remaining mineral content is not absorbed into the bloodstream, but is passed in the urine or faeces. Chelate-bound iron mineral supplements, in particular, can cause constipation as the chelate can act as a flocculent in the large intestine. It is desirable that such disadvantage be overcome in an alternative mineral 'delivery' system with improved bio-availability of the mineral elements.

Another mineral supplement composition is based upon a mineral salt combined with an organic glutamate binder. One product based upon the glutamate bound mineral delivery system is a lozenge containing zinc for oral ingestion. However, not only does the glutamate delivery system demonstrate restricted mineral element/ion bio-availability in similar fashion to the chelates described above, but also zinc glutamate lozenges in particular tend to leave undesirable coloured stains in the mouth. Accordingly it is also desirable to overcome this particular disadvantage in an alternative mineral delivery system providing better mineral element bio-availability.

In consequence it can be summarised that the existing chelate and glutamate bound mineral compositions deliver such mineral elements into the bloodstream but only a small proportion of the total content of the respective mineral element, and over a relatively lengthy period of time whereby specific mineral bio-availability is limited.

The present inventor has considered the existing mineral delivery systems such as the chelate and glutamate delivery systems and their disadvantages. The present invention provides inter alia, alternative mineral delivery systems based on quite different components which have been found to improve specific mineral bio-availability in terms of not only bloodstream quantities but also bloodstream absorption time.

The present inventor provides several aspects to his invention, based upon mineral or other metallic element—containing compositions, methods for preparing such compositions and uses of such compositions which encompass several distinct technical fields apart from the field of mineral supplements for the human or animal diet, namely uses of the compositions for medical conditions in the treatment of a disease or disorder, treating or purifying water or sewage, use as an algaecide, fungicide and disinfectant and uses in treating metal substrates to control corrosion.

Accordingly in a first aspect of this invention there is provided a metal-containing composition substantially comprising:

(i) at least one water soluble metal compound which forms metal ions when dissolved in water,
(ii) at least one metal ion modifier as herein defined,
(iii) at least one acid, and
(iv) water said composition having a pH of less than 6 and an electrolytic potential in excess of 10 millivolts.

The term 'metal' is used herein to encompass semi-metals of a mineral nature, e.g. selenium.

Such compositions preferably essentially consist of the aforesaid components with any preferred additives and more preferably consist of such ingredients, optional additives and the balance being any inevitable impurities.

In a second aspect of this invention there is provided a method of making a composition as defined in the first aspect comprising dissolving (i) in distilled water, adding (ii) and mixing or allowing to dissolve, then adding (iii) whilst simultaneously monitoring the pH and electrolytic potential of the composition until a required value of each measurement is obtained.

A third aspect of this invention provides the use of a composition as defined in the first aspect in medicine, for example the use of such a composition for preventing or treating one or more of the following pathogenic disorders, namely bacterial, fungal or viral infection, retroviral infection such as AIDS or Hepatitis C, particularly including copper containing such compositions for treating one or more of the following diseases, namely cholera, salmonella, shigella, *E. Coli* and chlamydia.

A fourth aspect of this invention provides the use of a composition as defined in the first aspect, in the preparation of a medicament for use in the treatment of a disease or disorder, such as one or more of the aforementioned diseases or disorders.

The invention also provides in a fifth aspect the use of a composition as defined in the first aspect in the treatment of water or water containing materials or sewage, effluent, commercial, domestic waste products as a bactericide, or algaecide, flocculent viricide and/or fungicide.

A sixth aspect of the present invention provides the use of a composition as defined in the first aspect to form a corrosion resistant coating or plating for metal substrates, to act as a sealant against metal corrosion.

In a seventh aspect the present invention provides the use of a composition as defined in the first aspect as a bactericidal and/or fungicidal preservative against the bacterial or fungal deterioration of edible foodstuffs.

The metal ion modifier is preferably a binder other than chelate or glutamate effective to transport ions incorporating the metallic mineral element through the digestive system and into the bloodstream in bioavailable form. Such binder can be, for example, a complexing, buffering or sequestering agent. It is most preferred to use soluble ammonium compounds, such as one or more of the following ammonium salts: ammonium chloride, sulphate or phosphate.

Such metal ion modifiers appear particularly effective in retaining and sustaining electrolytic potential.

The present invention is based on the inventor's discoveries that an improved metallic mineral delivery system for the human or animal bloodstream and other uses can be formulated from selected metal-containing electrolytes in acidic aqueous media which demonstrate a measurable electrolytic potential which is stable for a significant period of time. Such compositions have surprisingly been found, inter alia, when ingested or absorbed to make the mineral ions more rapidly available to the body for cellular uptake, and more efficiently and sustainably in terms of percentage by weight of bio-available mineral within the bloodstream, after a given time. Additionally it would appear that the ions incorporating the metallic mineral element are more bio-active due to enhanced beneficial effects which have been observed. The ions incorporating the metallic mineral element appear to be polarised, with an overall cationic charge. Accordingly, within the present compositions, the metallic element effects appear to be synergistically improved by the metal ion modifier. In particular this appears to be the case with zinc and magnesium compositions.

In preferred embodiments of the invention, the metal compositions are mineral metal such compositions and can act transdermally by passing through the skin, mucosa or other mucous membrane, for even more rapid absorption into the bloodstream.

Preferred embodiments of the compositions for dietary supplement or medical uses can provide up to 90% by weight of the mineral element absorbed into the bloodstream, in bio-available and potentially more bio-active form in up to 10 minutes e.g. within 6 to 10 minutes. Accordingly such compositions for dietary or medical uses in the form of acidic aqueous electrolyte solutions can provide for rapid mineral element ion delivery to the body for cellular uptake, with less wastage of the desirable mineral passing in the urine and/or faeces.

In the case of preferred compositions which contain iron or zinc as the mineral element, it is possible to avoid the disadvantages of chelated iron and zinc glutamate mentioned above, whilst simultaneously providing more of these mineral elements available in the bloodstream in less time and again apparently in a more bio-active form.

The present compositions for human or animal dietary or medical use are preferably based upon the presence of at least one water soluble metal compound such as a mineral metal salt in aqueous compositions which further contain components as defined in the first aspect and all of which said components have been designated GRAS (generally regarded as safe) food additives or other chemicals by the US-FDA.

In order to make the present compositions for human or animal dietary or medical use, it is preferred for the following general preparative procedure to be adopted:

General Procedure (a) The required metal such as a mineral element e.g. zinc is included by way of a soluble salt of the metal such as zinc sulphate. This is to be completely dissolved in distilled water (in contrast to deionised water) preferably 1 liter by mixing the salt into the water at ordinary room temperature, e.g. about 20° C. by vigorous stirring. The corresponding metallic mineral ions thereby form in the aqueous solution.

(b) When all the metallic salt has been completely dissolved in the distilled water, at least one metal ion modifier is added, preferably a sequestering, buffering or complexing agent such as one or more soluble ammonium salts, for example one or more of: ammonium sulphate, ammonium chloride, ammonium citrate, and ammonium phosphate, which is mixed into the solution to dissolve therein.

(c) To the aqueous mixture, obtained in step (b), at least one acid component (e.g. sulphuric and/or citric acid or hydrochloric acid) is added carefully and slowly, preferably by measured metering, to lower the pH of the mixture to a preferred level and to simultaneously exhibit a measurable electrolytic potential until a preferred level thereof is also reached. The value of electrolytic potential is preferably measured and monitored by milli-voltmeter. Several commercially available instantaneous readout pH meters can function as a milli-voltmeter by simple adjustment. Sufficient acid should be added so as to control the values of pH and electrolytic potential. This process for making the aqueous metal-containing compositions, particularly mineral metal such compositions for dietary or medical use, can be likened to a form of electrometric titration.

The inventor has observed that in many embodiments, after completion of step (c)—the addition of one or more appropriate acids, most preferably GRAS designated acids, the compositions exhibit behaviour associated with dynamic equilibrium solutions at relatively high electrolytic potential. An exothermic reaction during step (c) may be observed. The aqueous compositions in many embodiments also appear to demonstrate the characteristics of an overall cationic solution in which positively charged cations including the metallic element outnumber the anions. Furthermore such cations when present in the bloodstream appear to be attracted to and thereby damage or destroy pathogenic cells having an overall negative charge, such as bacterial, fungal or viral cells.

In order that the invention in all its aspects may be further elucidated a plurality of non-limiting examples are now presented in tabular form for a more complete appreciation of the invention, and to enable these and other embodiments of the invention to be reduced to practice by one of ordinary skill in the art. The preparative procedure in each example corresponds to the general procedure already outlined above, using 1 liter of distilled water, or 860 mls in the case of example 13a.

For the medical fields of application, the formulations can be administered orally in the range of 1 drop to 15 drops, dissolved in more water, once, twice or three times daily, depending upon the severity of the condition.

For the non-medical fields of application, the quantities to be used can be varied according to economics, effects desired, volume of material (eg water) to be treated. The precise amounts are rather less critical and adjustments can be made by the user.

It will be appreciated that where the metal compound is a sulphate, then the metal ion modifier is preferably also a sulphate and the acid preferably is sulphuric.

Similarly where the metal compound is a chloride, the ion modifier is preferably also a chloride and the acid is preferably hydrochloric. Where the metal ion modifier is a phosphate, it is preferred to use phosphoric acid as the acid, whatever metal salt is used as the source of metallic ions.

| Example No. | Mineral or other Metal Element(s) in Composition | Compound(s)/ Amount | Metal ion Modifier(s)/ Amount | Acid(s)/ Amount | Optional Additive(s) | Final pH | Final Electrolytic Potential Millivolts (mV) | Field(s) of Application |
|---|---|---|---|---|---|---|---|---|
| 1 | Copper | Copper Sulphate 150 g | Ammonium Sulphate 75 g | Sulphuric 98% 37.5 mls | — | <1.5 | 350–380 | Medical, Anti-bacterial especially against *Helicobacter pylori* |
| 2 | Copper | Copper Sulphate 150 g | Ammonium Sulphate 75 g | Sulphuric 98% variable* | — | 1–2 | >300 | Medical, anti mycological Treatment |
| 3 | Copper | Copper Sulphate 150 g | Ammonium Sulphate 75 g | Sulphuric 98% variable | — | <2 | >350 | Medical arthritis Alleviation |
| 4 | Copper | Copper Sulphate 200 g | Ammonium Sulphate 75 g | Sulphuric 98% variable | — | 1.5 | >350 | Substantial copper dietary supplement |
| 5 | Magnesium | Magnesium Sulphate/ 150 g | Ammonium Sulphate 75 g | Sulphuric 98% variable | Vitamin B1 Vitamin B3 | 1–2 | >350 | Medical, antiviral |
| 6 | Magnesium | Magnesium Sulphate/ 150 g | Ammonium Sulphate 75 g | Sulphuric 98% variable | — | 1–2 | >350 | Medical asthma treatment or prevention |
| 7 | Magnesium | Magnesium Sulphate/ 150 g | Ammonium Sulphate 75 g | Sulphuric 98% variable | — | 1–2 | >350 | Medical, stroke treatment and prophylactic |
| 8 | Magnesium | Magnesium Sulphate/ 150 g | Ammonium Sulphate 75 g | Sulphuric 98% variable | Malic acid | 1–2 | >350 | Medical, treatment for Chronic fatigue syndrome |
| 9 | Magnesium | Magnesium Sulphate/ 100 g | Ammonium Phosphate 60 g | Phosphoric Acid Concentrated 40 mls | Malic acid 40 g | 1–2 | >350 | As for example 8 and also for combatting side effects in patients with retroviral disease such as AIDS and/or Hepatitis C |
| 10 | Magnesium | Magnesium Sulphate/ 150 g | Ammonium Sulphate 75 g | Sulphuric 98% variable | Natural Diuretic | 1–2 | >350 | Medical relief of pre-menstrual tension |
| 11 | Magnesium | Magnesium Sulphate/ 150 g | Ammonium Sulphate 75 g | Sulphuric 98% variable | Melatonin Valerian | 1–2 | >350 | Medical treatment of insomnia |
| 12 | Magnesium | Magnesium Sulphate 200 g | Ammonium Sulphate 75 g | Sulphuric 98% variable | — | 1–2 | >350 | Substantial magnesium dietary supplement |
| 13 | Selenium | Selenium Sulphate 150 g | Ammonium Sulphate 75 g | Sulphuric 98% variable | — | 1–2 | >350 | Medical treatment of cancer |
| 13a | Selenium | Selenic Acid $H_2O_2Se$ 50 g | Ammonium Phosphate 80 g | Phosphoric Acid Concentrated 40 mls | — | 1–2 | >350 | Composition for use in the treatment of cancer. Hepatitis C and AIDS. Topical formulation of this composition has indications for treatment of melanoma |
| 14 | Iron | Iron Sulphate 200 g | Ammonium Sulphate 75 g | Sulphuric 98% variable | — | 1–2 | >350 | Substantial iron dietary supplement |
| 15 | Zinc | Zinc Sulphate 150 g | Ammonium Sulphate 75 g | Sulphuric 98% variable | Vitamin C | 1–2 | >350 | Medical, antiviral, particularly anti-retroviral eg Aids & Hepatits C |
| 16 | Zinc | Zinc Sulphate 200 g | Ammonium Sulphate 75 g | Sulphuric 98% variable | Stimulants - caffeine, Nicotine and ginseng | 1–2 | >350 | Medical, altertness enhancer, potential hangover remedy |
| 17 | Zinc | Zinc Sulphate 150 g | Ammonium Sulphate 75 g | Sulphuric 98% variable | — | 1–2 | >350 | Substantial zinc dietary supplement |
| 18 | Zinc | Zinc Sulphate 200 g | Ammonium Sulphate 75 g | Sulphuric 98% Variable | Vitamin B5 Vitamin B6 To accelerate Zinc Delivery | 1–2 | >350 | Medical - to counter side Effects of chemotherapy |
| 18a | Zinc | Zinc Sulphate 100 g | Ammonium Sulphate 65 g | Phosphoric acid concentrated 40 mls | Citric acid 30 g (catalyst) and pyruvic acid 50 g (co-enzyme) | 1–2 | >350 | Same as example 43 a more preferred formulation, suitable for AIDS patients with mitochondrial dysfunction or otherwise damaged by reverse transcriptase inhibitors |

-continued

| Example No. | Mineral or other Metal Element(s) in Composition | Compound(s)/ Amount | Metal ion Modifier(s)/ Amount | Acid(s)/ Amount | Optional Additive(s) | Final pH | Final Electrolytic Potential Millivolts (mV) | Field(s) of Application |
|---|---|---|---|---|---|---|---|---|
| 19 | Copper | Copper Sulphate 150 g | Ammonium Phosphate 75 g | Phosphoric Acid Variable | — | 1–2 | >350 | Fungicide, soil sterilant to replace methyl bromide, transdermal fungicide |
| 20 | Copper | Copper Sulphate 150 g | Ammonium Chloride 75 g | Hydrochloric acid-concentrated variable | — | 1–2 | >350 | As example 1 |
| 21 | Copper | Copper Sulphate 150 g | Ammonium Chloride 75 g | Hydrochloric acid-concentrated variable | — | 1–2 | >350 | As example 3 |
| 22 | Copper | Copper Sulphate 150 g | Ammonium Chloride 75 g | Hydrochloric Acid-concentrated Variable | — | 1–2 | >350 | Medical, fungicide, oral and/or topical formulations |
| 23 | Zinc | Zinc Sulphate 150 g | Ammonium Chlordie 75 g | Hydrochloric Acid-concentrated Variable | — | 1–2 | >350 | Medical, antiviral |
| 24 | Copper | Copper Sulphate 200 g | Ammonium Sulphate 75 g | Sulphuric acid 98% variable | — | 1–2 | >350 | Water purification - disinfectant |
| 25 | Copper | Copper Sulphate 200 g | Ammonium Sulphate 75 g | Sulphuric acid 98% variable | — | 1–2 | >350 | Water treatment - algaecide |
| 26 | Copper | Copper Sulphate 200 g | Ammonium Sulphate 75 g | Sulphuric Acid 98% Variable | — | 1–2 | >350 | Water treatment - swimming pool disinfectant |
| 27 | Copper | Copper Sulphate 200 g | Ammonium Sulphate 75 g | Sulphuric Acid 98% Variable | — | 1–2 | >350 | Sewage treatment - disinfectant |
| 28 | Iron | Iron Sulphate 150 g | Ammonium Sulphate 75 g | Sulphuric Acid 98% Varibale | — | 1–2 | >350 | Water treatment - flocculent |
| 28a | Iron | Iron II Sulphate monohydrate 133.33 g ($FeSO_4 \cdot H_2O$) Molecular weight = 151.91 Fe content per mole = 55.85 Fe content = 36.76% by weight | Ammonium Sulphate 66.66 g | Sulphuric acid concentrated 99% 33.33 mls | — | 0.79 | 391 | Water treatment, flocculant, removal of organic matter |
| 28b | Iron | Iron II Sulphate Heptahydrate 200 g $FeSO_4 \cdot 7H_2O$ Molecular weight = 278.01 Fe content = 20.08% by weight | Ammonium Sulphate 100 g | Sulphuric acid concentrated 99% 50 mls | — | 0.17 | 385 | As example 28a |
| 28c | Iron | Iron III Sulphate monohydrate 200 g $Fe_2(SO_4)$. | Ammonium Sulphate 100 g | Sulphuric acid concentrated 99% 50 mls | — | 0.15 | 404 | As example 28a |
| 28d | Iron | Iron III Chloride 200 g $FeCl_3$ | Ammonium chloride 100 g | Hydrochloric acid 35 . 38% by volume, specific gravity 1.18 50 mls | — | −0.45 | 436 | As example 28a |
| 28e | Aluminium | Aluminium Chloride 300 g molecular weight 241.43 Al content | Ammonium Chloride 150 g | Hydrochloric acid 35–38% by volume, specific gravity 1.18 | — | −0.98 | 466 | As example 28a |

-continued

| Example No. | Mineral or other Metal Element(s) in Composition | Compound(s)/ Amount | Metal ion Modifier(s)/ Amount | Acid(s)/ Amount | Optional Additive(s) | Final pH | Final Electrolytic Potential Millivolts (mV) | Field(s) of Application |
|---|---|---|---|---|---|---|---|---|
| 29 | Copper | 26.98% by weight Copper Sulphate 150 g | Ammonium chloride 75 g | Hydrochloric acid- concentrated variable | — | 1–2 | >350 | As example 1 |
| 30 | Copper | Copper Sulphate 150 g | Ammonium chloride 75 g | Hydrochloric acid- concentrated variable | — | 1–2 | >350 | As example 26 |
| 31 | Copper | Copper | Ammonium chloride 75 g | Hydrochloric acid- concentrated variable | — | 1–2 | >350 | Sewage treatment - disinfectant for sewage solids |
| 32 | Copper | Copper Sulphate 150 g | Ammonium Sulphate 75 g | Sulphuric 98% variable | — | 1–2 | >350 | Food preservation fungicide spray for fruit and vegetables |
| 33 | Copper | Copper Sulphate 150 g | Ammonium Sulphate 75 g | Sulphuric 98% variable | — | 1–2 | >350 | Food preservatiion - meat disinfectant |
| 34 | Copper | Copper Sulphate 150 g | Ammonium Sulphate 75 g | Sulphuroc 98% variable | Fructose | 1–2 | >350 | Flower, tree and shrub preservation e.g. christmas trees - bactericide and fungicide |
| 35 | Copper | Copper Sulphate 150 g | Ammonium Sulphate 75 g | Sulphuric 98% variable | — | 1–2 | >350 | Food preservation seafood preservative |
| 36 | Copper | Copper Sulphate 150 g | Ammonium Sulphate 75 g | Sulphuric 98% variable | — | 1–2 | >350 | Food preservation - for fruit and vegetables |
| 37 | Copper | Copper Sulphate 150 g | Ammonium Chloride 75 g | Hydrochloric acid- concentrated variable | — | 1–2 | >350 | Food preservation - food processing area sanitiser |
| 38 | Copper | Copper sulphate 300 g | Ammonium sulphate 82.5 g | Sulphuric 98% variable | — | 1–2 | >350 | Metal preservation - metal sealing, plating and anti- corrosion |
| 39 | Nickel | Nickel sulphate 300 g | Ammonium sulphate 82.5 g | Sulphuric 98% variable | — | 1–2 | >350 | As example 38 |
| 40 | Nickel | Nickel sulphate 200 g | Ammonium sulphate 75 g | Sulphuric 98% variable | Zinc sulphate | 1–2 | >350 | Industrial-algaecide and bactericide particularly in cooling towers to inhibit legionella bacteria |
| 41 | Titanium | Titanium sulphate 300 g | Ammonium sulphate 82.5 g | Sulphuric 98% variable | — | 1–2 | >350 | As example 38 |
| 42 | Vanadium | Vanadium sulphate 300 g | Ammonium sulphate 82.5 g 1 | Sulphuric 98% variable | — | 1–2 | >350 | As example 38 |
| 43 | Zinc | Zinc sulphate 150 g | Ammonium phosphate 75 g | Phosphoric acid varibale | Citric Acid | 1–2 | >350 | Medical, for use in repairing impaired/damaged mitochondria e.g. in patients with AIDS presently taking more than one AIDS treatment drug. |
| 44 | Magnesium | Magnesium sulphate 150 g | Ammonium phosphate 75 g | Phosphoric acid variable | Malic Acid | 1–2 | >350 | Medical, for use in repairing impaired/damaged mitochondria e.g. in patients with AIDS presently taking more than one AIDS treatment drug. |
| 45 | Zinc | Zinc sulphate 150 g | Ammonium phosphate 75 g | Phosphoric acid variable | Citric acid And Pyruvic acid | 1–2 | >350 | Medical - for use in treating ME chronic fatigue Syndrome |
| 46 | Magnesium | Magnesium sulphate 150 g | Ammonium phosphate 75 g | Phosphoric Acid variable | Malic acid | 1–2 | >350 | Medical - for use in treating ME chronic fatigue syndrome |

*N.B. variable denotes amount adjusted to obtain required specific pH and mV values, low pH and high mV being preferred.

From these examples it will be appreciated that the compositions may include one or more other additional components, besides the metal such as the preferred mineral, metal ion modifer, acid and water. By way of example, in zinc mineral compositions for dietary supplements or medical use it is preferred to incorporate one or more of the water soluble vitamins C. B5 and B6, each of which appear to play a role in accelerating delivery of the zinc mineral to cells via the bloodstream, to enhance the beneficial zinc ion effects.

In the case of magnesium mineral compositions for treating or preventing viral infections, it is preferred to include vitamins B1 and B3 to promote or synergise such beneficial anti-viral properties of the magnesium ion.

In the case of magnesium mineral compositions for treating chronic fatigue syndrome, it is preferred to include malic acid because it is useful for the same purpose. Compositions based on magnesium for treating PMT (pre-menstrual tension) preferably also include a natural diuretic to relieve water retention and for such compositions intended to treat insomnia, it is preferred also to include known sleep enhancers such as valerian or rapid eye movement extenders such as melatonin.

Zinc mineral compositions intended for enhancing vitality and for countering the effects of tiredness may further contain one or more of the following or other stimulants: caffeine, nicotine and ginseng.

The present compositions when used as a mineral source for rapid ingestion can demonstrate the following properties and advantages:

(1) An ability to bind metal ions, eg from salts through the action of at least one metal ion modifier within the acidic, electrolytically active aqueous solution. In this regard, the metal ion modifier appears to act as a binder and/or buffering agent which links up with the metal ions, and which 'buffers' those desirable metal ions against removal from the bloodstream.

(2) An ability to deliver and retain those mineral metals in an ionically modified form in the human or animal bloodstream through the buccal muscosa, oesophagus or stomach rapidly, i.e within a few minutes.

(3) The ionically modified mineral metal ions appear to remain in the blood serum to facilitate bio-availability of the specific mineral metal for cellular uptake, and moreover certain effects which have been observed appear to indicate that it is not only the bio-availability which is enhanced, but also and quite surprisingly the bioactivity of the mineral. This could be due to the apparent stability of overall cationic charge of the ions incorporating the metal.

(4) The ionically modified mineral metal ions retain a net positive electrical charge which interacts with negatively charged virus, bacteria or fungal cells, forming a complex with these pathogens.

(5) The ionically modified mineral metal ions in solution carry and appear to have the ability to deliver an electrical charge. This charge coupled with the overall mineral metal delivery system and the selected mineral metals help to control pathogens (bacteria, fungi and virus) apparently by degrading their membranes, complexing the pathogens thereby rendering them inactive or otherwise unable to harm the host's body. In this regard the present mineral metal compositions when delivered into the bloodstream, help the body's natural immune system to fight infection.

(6) Substantially improved bio-availability of the mineral in the bloodstream after digestion or absorption in terms of mineral quantity and substantially reduced time for the mineral to become bio-available after digestion or absorption i.e. rapid absorption.

(7) Additional medical benefits have surprisingly been found above and beyond the known benefits of mineral supplements. The present compositions have a wide variety of uses in medicine as hereinbefore described and whilst such benefits have been shown applicable to the treatment of human disease, similar uses are proposed in the treatment of animals by way of using the present compositions as veterinary mineral supplements.

The present compositions may be formulated as aqueous solutions and presented for use and/or sale within dropper bottles for convenient addition to foodstuffs, beverages or to water for consumption. Alternatively the compositions can be applied directly to the buccal mucosa for even more rapid mineral metal absorption into the bloodstream.

Alternatively the compositions may be formulated as capsules containing a unit dose, or presented in tablet form after evaporating or freeze drying the compositons in such a manner that the pH and electrolytic potential can be substantially restored to the preferred values described herein by the presence of acid in the stomach.

In order that application of the invention may be demonstrated, reference is now made to the accompanying drawings and the following non-limiting examples.

FIG. 1 shows the antibacterial activity of Example 24 against *Escherichia coli* QC strain at a variety of dilutions. Exposure was for one hour at 37 degrees centigrade. Under these testing conditions, a dilution of as little as 0.04 ppm was still effective in reducing bacterial counts by 99.9%. Recommended dosage is at the 1 ppm level.

| Actual Data: | |
| --- | --- |
| Control: (0 ppm) | $9 \times 10^4$ cfu/ml (colony forming units/milliliter) |
| 1.0 ppm: | No recoverable bacteria |
| 0.2 ppm: | No recoverable bacteria |
| 0.04 ppm: | 12.7 cfu/ml |
| 0.008 ppm: | $1 \times 10^4$ cfu/ml |
| 0.0016 ppm: | $6.4 \times 10^5$ cfu/ml |

Figure 2:
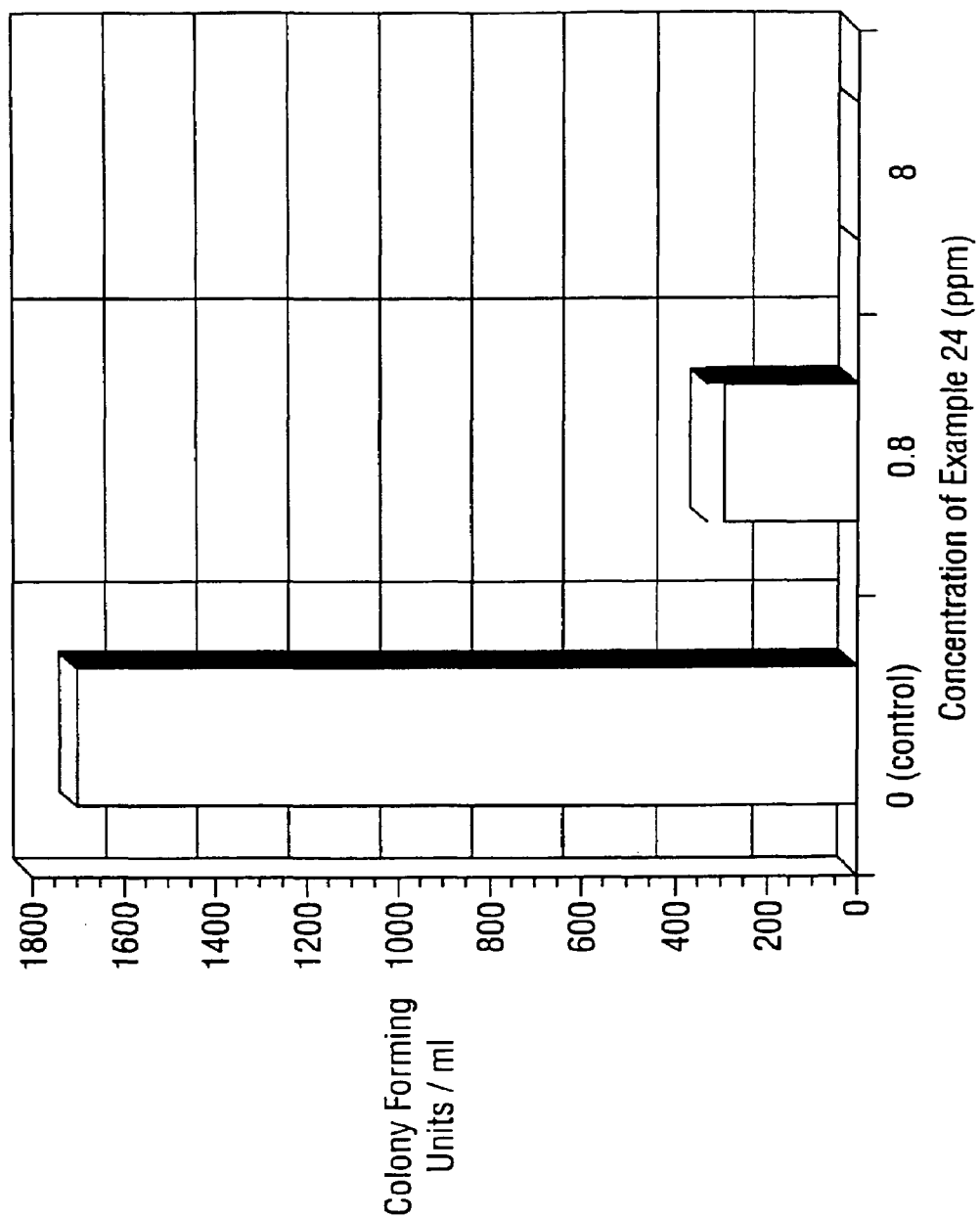

FIG. 2 shows the results of treating a treatment plant effluent with a formulation according to Example 24, wherein the colony forming units plotted are of residual fecal coliforms. The conditions leading to these results were as follows:

| 1 hour Exposure Time, 22 Degrees Centigrade Typical Effluent Conditions, Mg/L: | |
| --- | --- |
| Dissolved Oxygen | 4.8 |
| COD | 106 |
| pH (max) | 7.5 |
| pH (min) | 7.1 |
| Ammonium (NH3-N) | 9.0 |
| Total N (Kjeldahl) | 9.4 |
| Nitrogen Species (NOx) | 3.8 |
| BOD | 12 |

Figure 3:
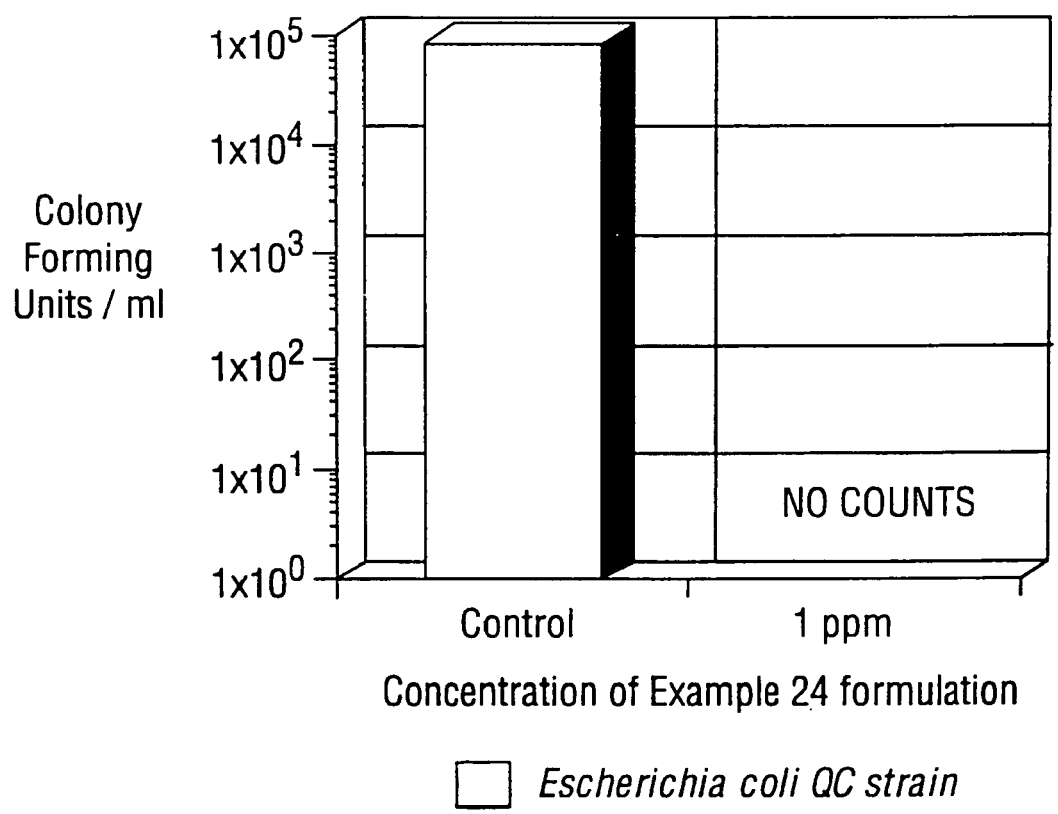

FIG. 3 shows the antibacterial activity of an example 24 formulation against *Escherichia coli* QC strain at a 1 ppm concentration. Exposure was for one hour at 37 degrees centigrade in 1 mM $PO_4$ buffer.

| Actual Data: | |
|---|---|
| Control: (0 ppm) | $9 \times 10^4$ cfu/ml |
| 1 ppm: | No recoverable bacteria |

Figure 4:
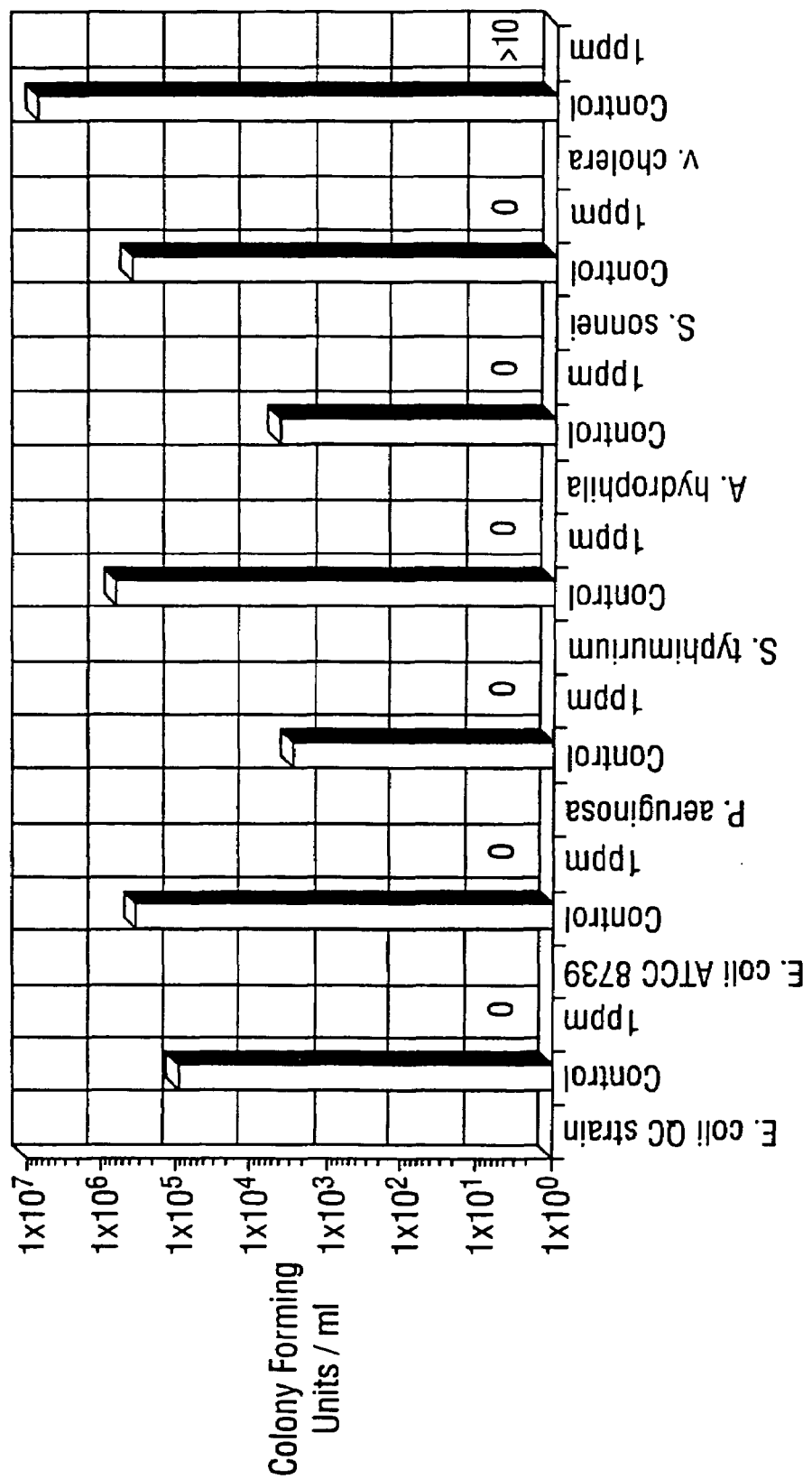

Further results against a variety of bacteria using a formulation corresponding to Example 24 are shown in FIG. 4. The conditions were broadly similar to those described with reference to FIG. 3.

The figures demonstrate the bacteriocidal activity.

The invention claimed is:

1. A metal-containing composition consisting essentially of:
   (i) at least one water soluble metal compound which forms metal ions when dissolved in water which consists of at least one compound selected from the group consisting of:
   zinc, magnesium, copper, selenium, iron, nickel, titanium, vanadium and aluminum compounds,
   (ii) at least one metal ion binding, complexing or sequestering agent other than chelate or glutamate selected from the group consisting of ammonium sulphate, ammonium chloride, ammonium phosphate and ammonium citrate,
   (iii) at least one acid selected from the group consisting of sulphuric, hydrochloric, phosphoric and citric acids, and
   (iv) water
   said composition having a pH of less than 3 and an electrolytic potential in excess of 50 millivolts.

2. A composition as claimed in claim 1 wherein said metal ion is at least one selected from the group consisting of the following mineral metals: copper, magnesium, selenium, iron and zinc.

3. A composition as claimed in claim 1 which consists of (i)–(iv) as defined in claim 1.

4. A composition as claimed in claim 1 wherein (i) is an inorganic salt of at least one selected from the group consisting of zinc, magnesium, copper, selenium, iron, nickel, titanium or vanadium.

5. A composition as claimed in claim 4 in which said salt (i) is at least one salt selected from the group consisting of sulphate, chloride and nitrate.

6. A composition as claimed in claim 4 in which said salt (i) is at least one salt selected from the group consisting of zinc, magnesium, copper, iron and selenium salts.

7. A composition as claimed in claim 6 in which (i) is a sulphate selected from the group consisting of zinc sulphate, magnesium sulphate, iron sulphate and copper sulphate.

8. A composition as claimed in claim 1 wherein (ii) is ammonium sulphate.

9. A composition as claimed in claim 1 wherein (iii) is sulphuric or hydrochloric acid.

10. A composition as claimed in claim 1 in which the pH value is less than 2.5.

11. A composition as claimed in claim 10 in which the pH value is 2 or less.

12. A composition as claimed in claim 1 in which the electrolytic potential is in excess of 100 millivolts.

13. A composition as claimed in claim 12 in which the electrolytic potential is in excess of 200 millivolts.

14. A composition as claimed in claim 13 in which the electrolytic potential is in excess of 300 millivolts.

15. A composition as claimed in claim 14 in which the electrolytic potential is in the range of 340 to 400 millivolts.

16. A method of making a composition as claimed in claim 1 comprising dissolving (i) as defined in claim 1 in distilled water, adding (ii) as defined in claim 1 and mixing or allowing to dissolve, then adding (iii) as defined in claim 1 whilst simultaneously monitoring the pH and electrolytic potential of the composition until a required value of each measurement is obtained.

17. A method as claimed in claim 16 in which (i) is an inorganic salt of at least one compound selected from the group consisting of zinc, magnesium, copper, selenium, iron, nickel, titanium or vanadium.

18. A method as claimed in claim 16 in which (ii) is ammonium sulphate.

19. An antimicrobial, antiviral, antiretrovirus or antifungal formulation comprising a composition as claimed in claim 1 in conjunction with a pharmaceutically acceptable carrier, diluent or excipient therefor.

20. A composition as claimed in claim 10 which the pH value is in the range of 1 to 2.

21. A composition as claimed in claim 14 in which the electrolytic potential is at least 340 mV.

* * * * *